United States Patent [19]

Dalla Favera

[11] Patent Number: 4,997,764
[45] Date of Patent: Mar. 5, 1991

[54] TRANSFORMATION OF HUMAN B-LYMPOCYTES WITH EPSTEIN BARR VIRUS AND C-MYC CONTAINING VECTORS

[75] Inventor: Ricardo Dalla Favera, New York, N.Y.

[73] Assignee: New York University, New York, N.Y.

[21] Appl. No.: 41,803

[22] Filed: Apr. 23, 1987

[51] Int. Cl.$^5$ .................. C07K 15/28; C12N 5/22; C12N 5/24; C12N 15/85
[52] U.S. Cl. ................. 435/240.27; 530/387; 530/809; 530/808; 530/828; 435/70.21; 435/69.6; 435/172.2; 435/172.3; 435/240.21; 435/240.2; 435/240.26; 435/320.1; 935/32; 935/34; 935/57; 935/71; 935/93; 935/100; 935/108; 935/109
[58] Field of Search ............ 435/240.27, 6, 68, 172.3, 435/172.2, 240.2, 240.21, 240.26, 320; 530/387, 806, 808, 809; 935/32, 34, 57, 71, 93, 100, 108, 109

[56] References Cited

U.S. PATENT DOCUMENTS 4,701,409 12/1987 Croce ..................................... 435/91
4,740,461 4/1988 Kaufman ............................... 435/68

OTHER PUBLICATIONS

Lombardi et al., Cell, 49, 161-170, Apr. 24, 1987.
Kessler et al., Canc. Res., 47, 527-531, (Jan. 1987).
Dalla Favera et al., NYAS, vol. 511, "Normal and Neoplastic Blood Cells; From Genes to Therapy", Disclosed Jun. 10-13, 1986 (Rome, Italy) published 1987, New York.
Wennborg et al., Int. J. Cancer, 40, 202-206, (1987).
Polack et al., Embo. J., 6(10), 2959-2964, 1987.
Van Meel et al., J. Immunol. Meth., 80, 267-276, (1985).

Primary Examiner—Margaret Moskowitz
Assistant Examiner—Jeff Kushan
Attorney, Agent, or Firm—Darby & Darby

[57] ABSTRACT

Disclosed herein is a method for transforming human B-cells by infecting them with Epstein Barr virus and transfecting the Epstein Barr virus infected cells with an activated human c-myc gene. The transformed cells are useful for producing human monoclonal antibodies.

5 Claims, 7 Drawing Sheets

TRANSFORMATION OF HUMAN B-LYMPOCYTES WITH EPSTEIN BARR VIRUS AND C-MYC CONTAINING VECTORS

BACKGROUND OF THE INVENTION

This invention relates to a method for the production of transformed human cells that can be used for the production of human monoclonal antibodies and can also be employed to transform any mamalian cell.

Since its introduction in 1975, the well-known Kohler and Milstein technique (Nature 256:495, 1975) for the production of mouse hybridoma cells has made it possible to produce large quantities of mouse antigen-specific monoclonal antibodies that are useful in a number of investigative, diagnostic and therapeutic applications. The mouse hybridoma cells, which arise from the fusion of antibody-producing cells (B-lymphocyte cells, hereinafter referred to as B-cells) with malignant, transformed B-cells (in vivo transformed, myeloma cells from mice afflicted with myeloma or plasmacytoma) are capable of producing large quantities of monoclonal antibodies with predetermined specificities.

Using the Kohler and Milstein technique, a B-cell and a plasmacytoma cell are fused using, for instance, polyethylene glycol, lysolecithin or sendai virus as the cell fusing agents. A selectable marker must be present in the fused cells to enable them to be selected from parent cells and other non-hybridoma cells. As an example, the plasmacytoma fusion partner is generally deficient in an enzyme, (for instance, hypoxanthineguanosyl phosphoribotransferase (HGPRT)) that is necessary for growth of the fused cell in certain media (hypoxanthine, aminopterin, thymidine containing medium or HAT medium). This enzyme deficiency enables the resultant hybrids to be selected for their ability to grow in such media. This insures that only B-cell: plasmacytoma cell hybrids are recovered since neither parental cells (and hybrids comprising B-cell: B-cell and plasmacytoma: plasmacytoma cell) can survive in HAT medium.

The mouse antibodies produced with the Kohler and Milstein technique cannot be administered to human subjects for use as in-vivo therapeutic agents, e.g., to provide passive immunity to an infectious agent. The extension of the Kohler and Milstein hybridoma technology to the production of human monoclonal antibodies has been limited due to: (1) the lack of good human plasmacytoma cells for fusion partners; (2) the low frequency of cell fusion events; and (3) the relative scarcity of circulating B-cells producing specific antibodies against antigens of interest (and the inherent difficulties in isolating such cells). These factors make it difficult to obtain hybridoma cell lines secreting human monoclonal antibodies of a predetermined specificity.

Casali et al (Science 234:476–479, 1986) disclose a method which represents a step toward making human monoclonal antibody-producing cells. Normal B-cells obtained from peripheral human blood, were preselected for their specificity to a given antigen by Fluorescence-Activated Cell Sorting (FACS). Positively selected clones were then established as lymphoblastoid cells in vitro by infecting such cells with Epstein-Barr virus (EBV). The EBV infected cells produced antigen-specific human monoclonal antibodies. However, the method of Casali et al has the following drawbacks: (1) the amount of monoclonal antibodies produced by the Casali et al cells is relatively low, and (2) the antibody producing cells are relatively unstable and some clones stop antibody production prematurely. In addition maintenance of the antigen-specific antibody production requires repeated cloning of the cells, a time-consuming and inefficient procedure given the low clonogenic (i.e. growth) properties of the resultant lymphoblastoid (LB) cells; (3) large-scale production and purification of the monoclonal antibodies is inefficient in view of the long doubling time and high serum requirements of the LB cells; and (4) the LB cells produced by this process cannot be grown as tumors in animals. Such tumor cell growth permits the amplification and purification of antibodies from ascitic fluids, an efficient method for large scale antibody production that is widely used in making murine monoclonal antibodies.

Currently there is no convenient and reliable system available for the production of human monoclonal antibodies wherein the monoclonal antibody-producing cells are stable, highly malignant cells which can be readily manipulated for the induction of high antibody titers.

SUMMARY OF THE INVENTION

The present invention provides a method and a cell line for producing human monoclonal antibodies. According to the method, human B-cells are isolated that produce an antibody for a specific antigen. The isolated human B-cells are infected with Epstein-Barr virus (EBV). The EBV infected B-cells are then transfected (transfection is the process of introducing DNA into cells) with activated c-myc DNA. The resultant Epstein-Barr virus infected human B-cells express a protein corresponding to the c-myc DNA nucleotide sequence. These tumorigenic cells are effective for producing human monoclonal antibodies.

Another aspect of the invention is a human transformed B-cell comprising a human B-lymphocyte infected with Epstein-Barr virus. The B-cell also contains a vector comprising the plasmid PBR322 containing DNA segments coding for (a) the Epstein-Barr virus origin of replication, (b) a selectable genetic marker, and (c) an activated c-myc gene. In one specific embodiment of the invention the activated c-myc gene lacks the first exon of the full c-myc gene and includes the enhancer/promoter region of the Simian virus 40 gene, in proper orientation and in the correct reading frame.

It, is therefore an object of the present invention to provide a method for the production of tumorigenic human cells that are capable of producing human monoclonal antibodies. A further object of the present invention is to provide a transformed lymphoblastoid cell that is useful as a fusion partner in the production of human monoclonal antibodies.

Another object of the present invention is to produce a new human cell line comprising human B-cells infected with Epstein-Barr virus and transfected with an activated c-myc plasmid.

These and other aspects of the present invention will be apparent to those of ordinary skill in the art in light of the present description, accompanying claims and appended drawings.

DETAILED DESCRIPTION OF THE INVENTION

This invention involves a method for producing transformed human cells. The method is particularly useful for transforming normal human B-cells into malignant transformed, monoclonal antibody-producing transformed cells. This is important and unexpected as heretofore it has not been possible to make viable human transformed B-cells using in vitro manipulations.

Whereas conventional hybridoma cells are the product of a fusion event using a transformed lymphoblastoid cell and a normal B-cell the method of the present invention requires only a normal human B-cell. Using the method of the invention, transformed human B-cells, capable of producing human monoclonal antibodies of any desired specificity can be readily and easily obtained.

The method of the present invention involves selecting a human B-cell producing antibodies to a specific antigen, which may be predetermined. The selected B-cells are then infected with EBV. The EBV-infected B-cells are transfected with an activated c-myc plasmid and the fully transformed EBV-infected B-cells (EBV-myc-cell) are recovered.

In an alternative embodiment of the invention, the process described above is used to produce human transformed B-cells of predetermined antigenic specificity which can be used as fusion partners for the production of conventional human hybridoma cells. This is accomplished by fusing EBV-myc transfected B-cells (preselected for antigen specificity) to human myeloma cells. The resultant hybridoma cell is viable and capable of producing monoclonal antibodies.

EBV-infected B-cells demonstrate properties which are intermediate between normal human cells and malignant tumorigenic human cells. The EBV infected B-cells (LB cells) exhibit the ability to grow in tissue culture indefinitely in the presence of serum-containing medium. However, they lack the ability to produce colonies when grown in semi-solid medium (agar) and are unable to grow when injected into susceptible hosts, such as mice or rats. Therefore, the method of the present invention comprises transfecting EBV-infected human B-cells with a plasmid (hereinafter termed an activated c-myc plasmid) which confers upon the recipient cells these latter two properties.

The conversion of normal mammalian cells to the transformed state is associated with the activation of one or more oncogenes, each specific for a specific cell type. For example, the myc gene is that portion of the genome of the acute avian retrovirus MC29 that is responsible for its ability to induce a variety of tumors within weeks of its injection into newly hatched chicks. Thus, a cell can become transformed by a virus by acquiring the viral oncogene, such as v-myc, or having an apparently normal gene such as c-myc, overexpressed. The c-myc gene is activated in human B-cell tumors, such as Burkitts lymphoma and non-B-cell malignancies such as small cell carcinoma, breast cancer and leukemia, among others.

Normal human B-cells can be isolated from peripheral human blood using conventional methods that are well known to those in the art. The isolated B-cells can be selected for their ability to produce antibodies directed against any antigen using the method of Casali et al (supra) as described in Example 6 below. Once human B-cells that produce antibodies directed against a specific antigen have been isolated, they are infected with EBV (obtainable by culturing EBV-infected marmoset leukocyte cell line B95-8, available from the American Type Culture Collection (ATCC) as ATCC CRL 1612, ATCC, Rockville, Md) as described in Example 3 below. The amount of EBV needed is that which allows for a successful infection or, about one transforming unit per cell as described below.

In a particularly preferred embodiment, prior to EBV infection the specific antibody-producing human B-cells that have been obtained from the peripheral blood are screened and mature B-cells that produce IgG are identified and segregated. These IgG producing cells yield higher titers of antibodies directed against specific antigens then the less mature IgM-producing cells. Furthermore the IgG producing B-cells yield antibodies having a higher affinity for specific antigens. The isolated IgG producing B-cells may be used in practicing the method of the invention.

Most EBV-infected B-cells studied until now have been found to produce IgM. These IgG producing B-cells can be easily selected because they display differentiation-associated surface markers such as PCA-1 and B-1 (commercially available antibodies to these markers can be obtained from Coulter Immunology, Hilleah, Fla.) which can be selectively identified as shown in Example 2 below.

After the B-cells have been infected with EBV, the cells are transfected with an effective amount of an activated c-myc plasmid as discussed below. An effective amount for transfection is that which produces high levels of c-myc expression. An activated c-myc gene is defined as a c-myc gene which expresses a constitutive (i.e., not regulated) high level of the c-myc protein. High levels of this protein have been found to induce unrestrained cell division in human cells. For purposes of the invention the c-myc gene may be "activated" by (1) removal or mutation of "restraining" sequences present in the gene; or
(2) insertion of "enhancer" elements adjacent to said gene; or
(3) by a combination of these two procedures.

Any technique for introducing DNA into eukaryotic cells can be used for transfection of the plasmid materials in practising the present invention. Well-known techniques for plasmid transfection which can be used in practicing the present invention include, but are not limited to, microinjection, calcium phosphate precipitation, DEAE-dextran protoplast fusion or electroporation. Electroporation is preferred when using lymphoblastoid cells whereas other techniques may be more efficient when using different cell types. The most efficient technique for use with a given cell type can be determined by routine experimentation.

Microinjection involves the direct injection of plasmids into the nucleus of eukaryotic cells (as described in Capecchi, M. R., Cell 22:479–488, 1980). A drawback of this technique is that it requires sophisticated machinery for the delivery of very small volumes (nanoliters) and an operator with considerable technical expertise.

DEAE-dextran-mediated protoplast fusion employs a fusion event between the receipient cell and a bacteria carrying the plasmid of interest (Sandri-Goldin, R. M. et al Mol. Cell Biol. 1:743-752, 1981).

Calcium-phosphate precipitation induces uptake of DNA (or plasmids) into cells (Graham, F. L. et al, Virology 52:456-467, 1973) The plasmid is then translocated into the nucleus of these cells.

Electroporation involves exposing a cell suspension to a brief electrical impulse which results in the transfer of DNA into cells (Potter, H. L. et al., *Proc. Nat. Acad. Sci.*, USA 81:7161-7165, 1984). DNA entry is believed to occur via local areas of reversible membrane breakdown (or pores) created by the external electrical field.

The transfected EBV-myc cells of the present invention produce monoclonal antibodies, display a relatively short doubling time (on the order of about 27 hours), are clonogenic in semi-solid media and are tumorigenic in experimental animals. The in vitro transformation (i.e. generation of clonogenic and tumorigenic cells) of human B-lymphocytes has not been previously carried out in vitro.

The activated c-myc plasmids of the present invention termed pHEBoSVmyc 1,2,3, pHEBoSVmyc 2,3 and pHEBuSVmyc 2,3, are produced by standard cloning techniques, well-known in the art, as described in Examples 3 and 5 below. Plasmid pHEBoSVmyc 2,3 is preferred because it has been found to produce the largest number of tumorigenic EBV-myc cells. Although specific examples of plasmid vectors useful in practicing the invention are presented herein, it will be apparent to those skilled in the art that many different constructs can be employed. To be useful in practicing the present invention a vector must meet the following minimum requirements: (1) contain an activated c-myc gene capable of constitutive (i.e. non-regulated) expression and (2) possesses a selectable genetic marker (for example antibiotic resistance) for the positive selection of successful transfection and expression. In addition, the EBV origin of replication (oriP gene) is required for replication and expression of this plasmid in EBV-infected LB cells. The EBV origin of replication has been mapped to a segment of the viral DNA that is at least 800 basepairs (bp) and at most 1800 bp long (Yates, J. et al, Proc. Natl. Acad. Sci. USA, 81:3806-3810, 1984, incorporated herein by reference). This region confers efficient, stable replication to plasmid-transfected cells containing EBV genomes.

Plasmid pHEBo (described in Sugden et al. *Mol. Cell. Biol.*, 5:410-413, 1985), used in preparing the plasmids of the invention, contains the EBV origin of replication, oriP and the coding sequences for resistance to the antibiotic hygromycin B.

A selectable genetic marker is required to practice the invention. The marker is used to select for EBV-infected successfully myc-transfected cells. In this process of selection, only EBV-myc cells are able to grow while all other cells (i.e., non-transfected EBV-infected B-lymphoblastoid cells) are killed. Selectable genetic markers that can be used in the plasmids of the present invention include, by way of non-limiting example, resistance to an antibiotic substance, e.g., neomycin, G418, or hygromycin, or any other substance that confers a selective advantage to the transfected cells. Indeed, any selectable genetic marker which can be expressed in mammalian cells can be used in practicing the invention. Hygromycin resistance is the preferred genetic marker when using lymphocytes because non-hygromycin-resistant lymphocyte cells are killed by very low concentrations (50-300 micrograms per ml) of this aminoglycoside antibiotic, whereas hygromycin resistant normal lymphocytes are not. Hygromycin resistance is not a property of normal human lymphocytes. Human lymphoblastoid cells can be made hygromycin resistant by incorporation of a gene which inhibits the activity of this antibiotic. Such a gene can be isolated as described in Example 3 below.

Although specific plasmids for use in practicing the present invention are disclosed herein, practice of the invention is not limited to these plasmids. Among the other plasmids which may be used in practicing the invention are conventional plasmid vectors capable of integration into the host cell genome, or retroviral vectors (as described in Cepko et al. cell 37: 1053 (1985). The latter are particularly preferred because of their relative high efficiency of transfection. Because retroviral vectors do not require EBV infection for their expression, they can transfect a wider variety of cells, and result in a plasmid in which the c-myc gene is expressed.

The human c-myc gene is the cellular homolog of a viral transforming oncogene and is available from the ATCC (Accession No. 41010, American Type Culture Correction, Rockville, Md.) The c-myc gene comprises three exons (sequences present in mRNA after splicing, two of which are coding) and two introns (intervening sequences, removed during RNA splicing). A common property of plasmids that are useful in practicing the instant invention is the ability of these constructs to produce the high levels of the c-myc gene product required for the transformation of the EBV-infected B-cells to tumorigenic B-cells. The activation of the c-myc gene can be accomplished by the removal or mutation of normal regulatory sequence and/or by the insertion of an exogenous "enhancer" sequence in the plasmid DNA adjacent to the c-myc gene. Enhancer sequences have been isolated from the genome of certain tumor viruses (such as Simian Virus 40 (SV40), Banerji et al., *Cell* 27:299, 1981, and retroviruses, Llucin et al. *Cell* 33:705, 1983, among others) and from the genome of normal mamalian cells (such as the immunoglobulin gene enhancers, as described in Church et al., *Nature* 313:798, 1985). These sequences have been found to increase the expression of adjacent genes, and their presence in the c-myc plasmids of the present invention leads to the required deregulated expression. The deregulated c-myc gene is termed "activated". Any method suitable for the activation of the human c-myc gene can be used in practicing the methods of the present invention.

Another embodiment of the present invention comprises a method for transforming any mammalian cell. The method comprises transfecting the cell with a plasmid containing: (1) an activated c-myc gene capable of constitutive expression; (2) the EBV oriP gene; (3) the gene encoding the EBV nuclear antigen (EBNA); and (4) a gene encoding a selectable marker (i.e., antibiotic resistance). This embodiment avoids the necessity of infecting the transfected cells with EBV. This is of considerable value since many human cells cannot ordinarily be infected with EBV. The construction and the use of one such plasmid is illustrated in Example 5 below.

Cells which are EBV-infected will allow the growth of plasmids containing the EBV origin of replication (oriP) gene; non-EBV-infected cells will only express such a plasmid if the EBV oriP gene and the EBV nuclear antigen (EBNA) are present.

The c-myc containing EBNA plasmids of this embodiment of the invention would be particularly useful to transform T-lymphocyte cells (T-cells) for the purpose of making such cells immortal. For example, the resultant cells would be useful for lymphokine production (such as interleukin-2 and gamma-interferon), or for producing T-cells of predetermined antigenic specificity.

The present invention is further described below in specific examples which are intended to illustrate the invention without limiting its scope.

EXAMPLE 1: ISOLATION OF B-CELLS

Blood obtained from healthy males and females was placed on a gradient medium for separating lymphocytes (Pharmacia, Piscataway, N.J). Monocytes were removed from other mononuclear cells by two cycles of incubation at 37° C. in plastic 150cm$^2$ tissue culture flasks. The mononuclear fraction was incubated in ice with AET (2-aminoethylisothioronium bromide hydrobromide) (Sigma, St. Louis, Mo.) treated sheep red blood cells (SRBC) to allow for rosette formation. Nonerythrocyte rosette-forming cells (i.e. non-T-cells) were recovered after application of the whole SRBC mononuclear fraction to a lymphocyte-separating medium gradient. The nonadherent, nonrosetting fraction was constituted of at least 50% B-cells, less than .1% monocytes and variable amounts of lymphocytes.

EXAMPLE 2: EBV INFECTION OF CB33 CELLS

EBV used to infect normal human cord blood cells was obtained from culture fluids of B95-8 marmoset lymphoma cells (ATCC No. CRL 1612) in the presence of $1.62 \times 10^{-8}$M 4-phorbol-12 beta-myristate-13-alpha-acetate (TPA, Sigma Fine Chemical Company, St. Louis, Mo.). The virus preparation had a titer of $5 \times 10^5$ transforming units per ml, one unit being the minimum amount of virus-transforming $10^4$ purified human B-cells. Lymphocytes, at $1 \times 10^6$ per ml were exposed to the EBV-containing medium from B85-9 cells, at a multiplicity of infection of 1 transforming unit per cell.

The EBV-infected cells are then cultured for 3-4 weeks in culture medium (RPMI 1640, GIBCO, Grand Island, N.Y.) continuing 10% fetal calf serum.

EXAMPLE 3: PRODUCTION OF C-MYC PLASMID CONSTRUCTIONS

Enzymes (restriction endonucleases, ligases, Klenow fragments, etc) for use in constructing the plasmids of the present invention are commercially available from New England Biolabs (Beverly, Mass.), Boehringer Mannheim (Indianapolis, Ind.) and Bethesda Research Labs (Gaithersburg, Md.).

The plasmid pHyg which confers resistance to hygromycin B using transcriptional controls from the HSV-1 tk gene was constructed from pKan2 (Yates et al. *Proc. Nat. Acad. Sci.* USA 81: 3806–3810, 1984 and pLG89 (Gritz and Davies Gene 25: 179–188, 1983). pKan2 was digested with SmaI and BglII to remove the sequences derived from transposon Tn5. The hygromycin-resistance hph gene was inserted into the digested pKan2 using blunt-end ligation at the SnaI site and "sticky-end" ligation (using 1 Weiss unit of T$_4$ DNA ligase (BRL) in 20 microliter volume) at the BglII site. The SmaI and BglII sites of pKan2 were lost during ligation.

The plasmid pHEBo (B. Sugden et al *Mol. Cell. Biol.*, 5:410–413, 1985) which confers resistance to hygromycin B, carries the EBV oriP, and replicates as a plasmid in EBV-transformed cells, was constructed from pHyg and a plasmid carrying the BamC fragment of EBV pBamC (Yates et al., supra). pHyg was digested with BstEII and its end repaired using T$_4$ DNA polymerase (BRL). pBamC was digested with SphI and SstII and the fragment mapping from 7333 to 9516 bp on the EBV map was isolated and its end repaired with T$_4$ DNA polymerase. The EBV DNA was then blunt-end ligated into the digested pHyg to yield pHEBo. The BstEII, SphI, and SstII sites were all lost in this process.

Figure 1:
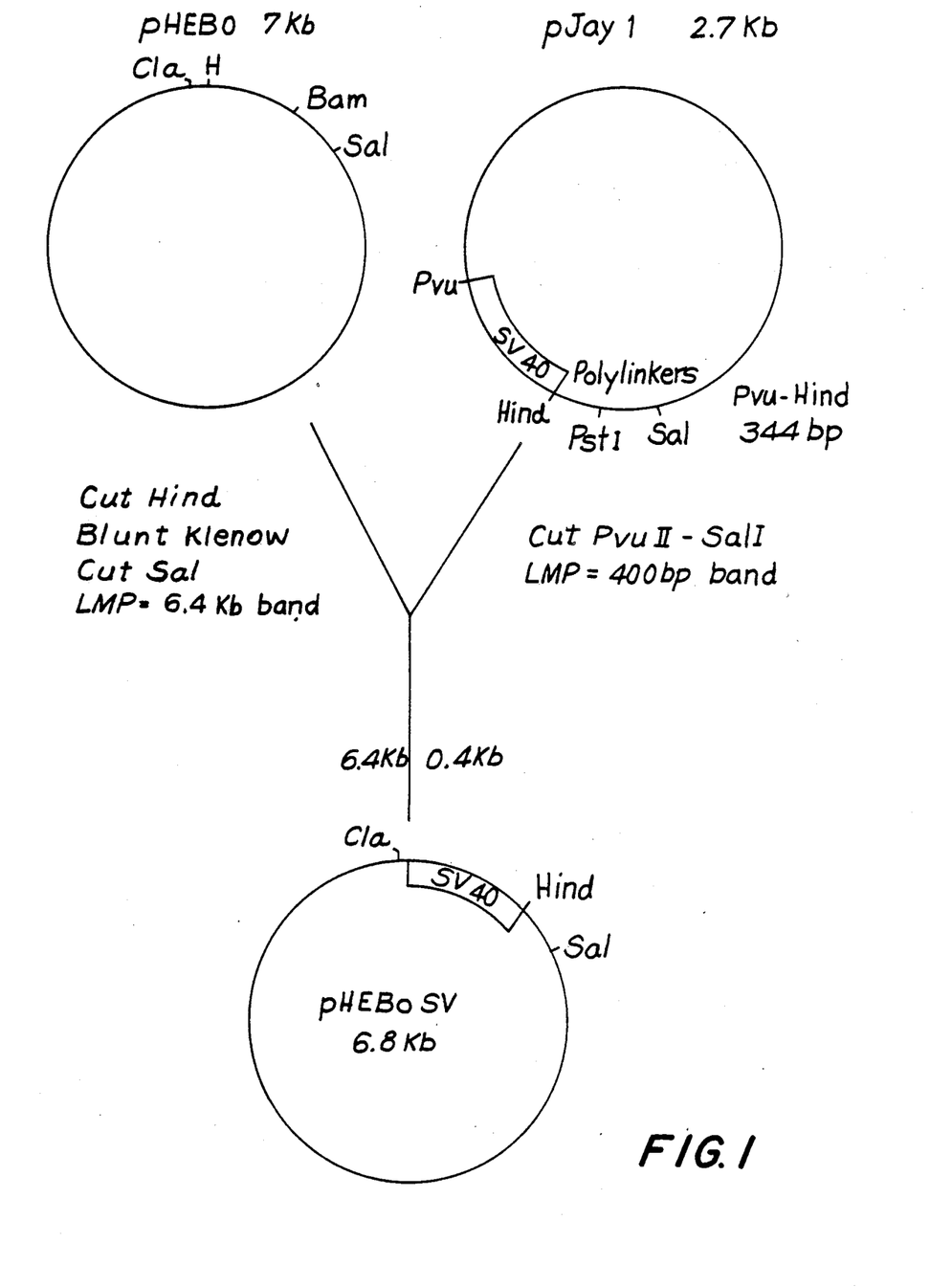
FIG. 1 is a schematic representation of the construction of plasmid pHEBoSV.
Figure 2:
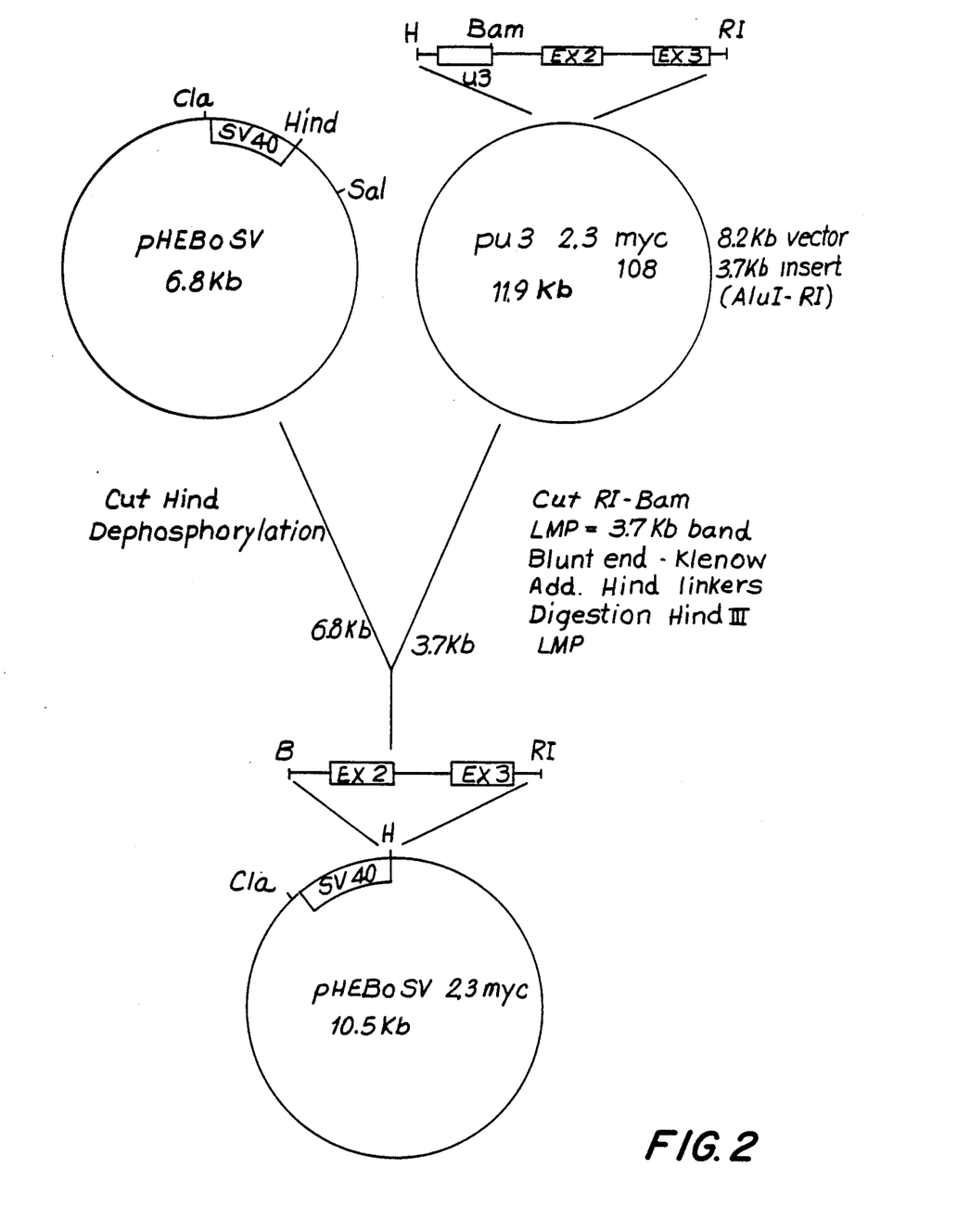
FIG. 2 is a schematic representation of the construction of plasmid pHEBoSVmyc 2, 3.
Figure 3:
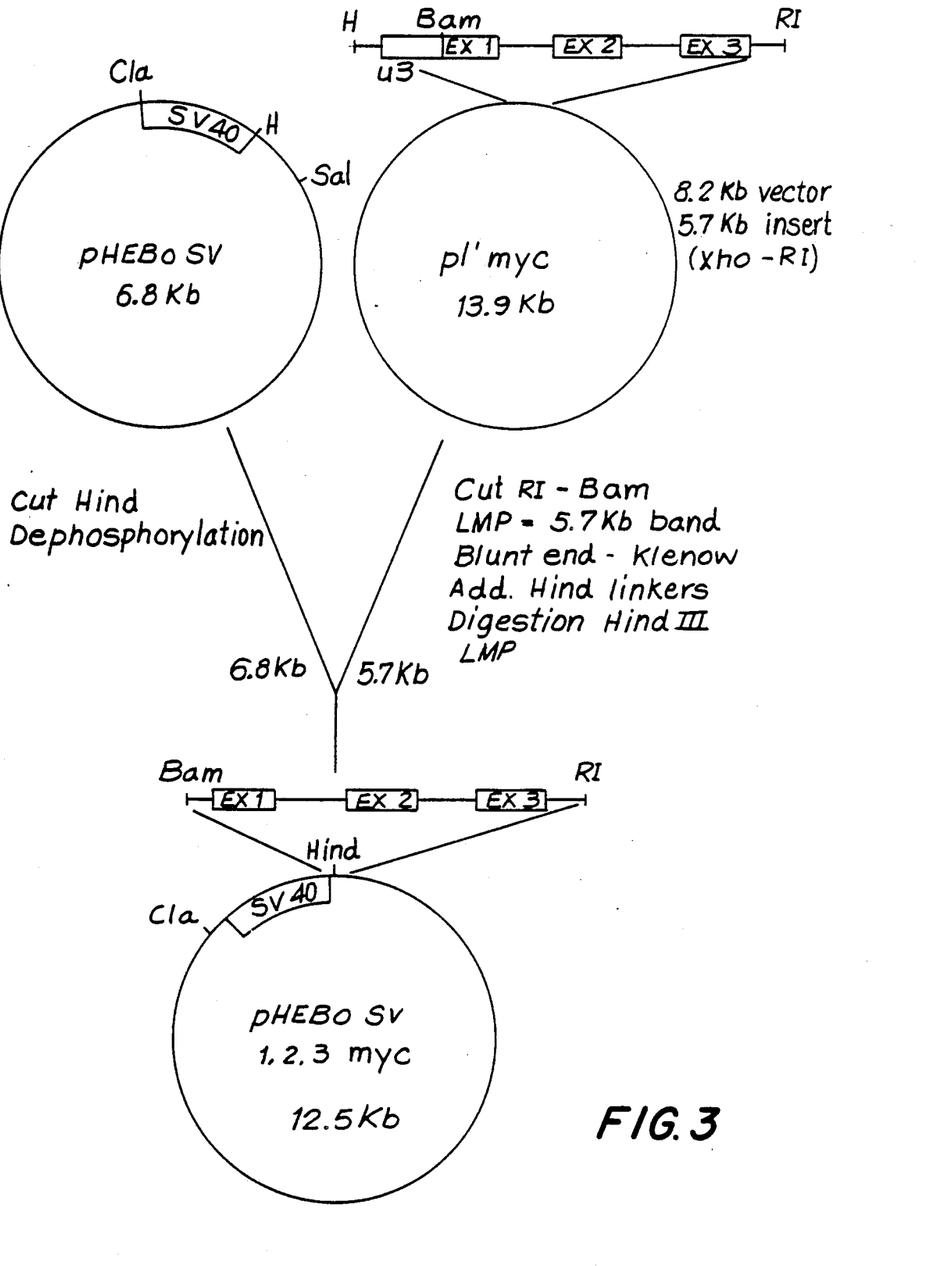
FIG. 3 is a schematic representation of the construction of plasmid pHEBoSVmyc 1, 2, 3.
Figure 4:
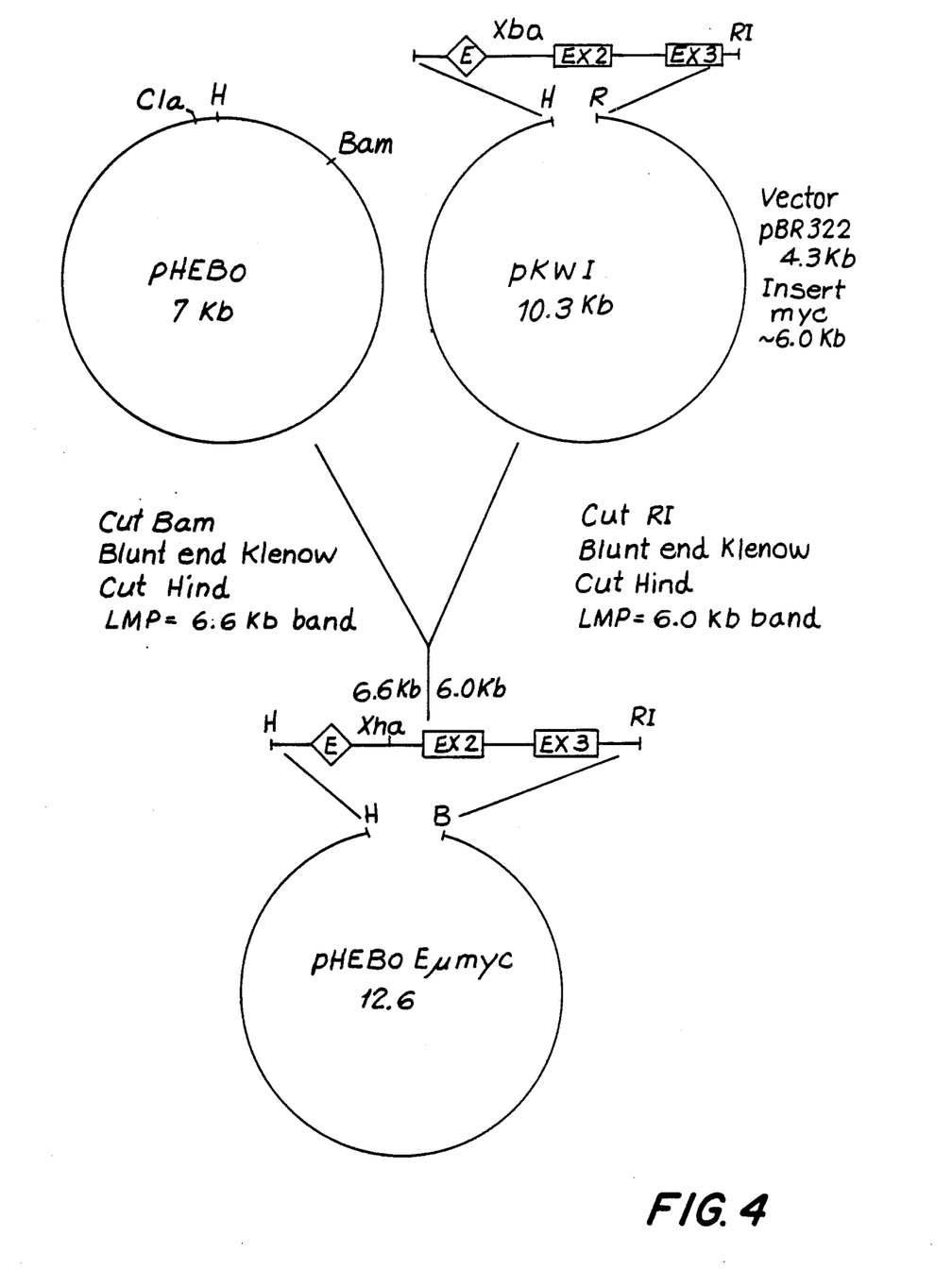
FIG. 4 is a schematic representation of the construction of plasmid pHEBoEumyc 2, 3.

The c-myc plasmids of the present invention (termed pHEBoSVmyc 1, 2, 3 and pHEBoSVmyc 2, 3) were generated as follows from pHEBo (Sugden et al., supra, See FIGS. 1, 2 and 3). An 0.4 kilobase (Kb) PvuII-SalI fragment containing the SV40 enhancer/promoter region upstream from a polylinker element, was isolated from the plasmid pJay 1 by PvuII—Sal I digestion of pJay 1 DNA followed by preparative electrophoresis in a low melting point agaroge gel. It was then ligated to the HindIII-SalI sites of pHEBo after blunt-ending of the HindIII sites with the Klenow fragment of DNA polymerase I (in 7mM Tris-HCL pH 7.5, 17mM MgCl$_2$ lmM dithiothreitol, 25 mM NaCl, 16 micromolar of each deoxynucleotide triphosphate, 1 microgram DNA and 1 unit of enzyme (BRL) in a 30 microliter volume for 15 minutes at 25 degrees C.) The resulting plasmid (pHEBoSV, See FIG. 1) was cut with restriction enzyme HindIII to accommodate a HindIII-linkered BamHI-EcoRI fragment from plasmid pU3 2, 3 myc containing a c-myc gene truncated in the first exon, to generate pHEBoSVmyc 2, 3 (See FIG. 2) and a HindIII-linkered BamHI-EcoRI fragment from plasmid pLIHmyc (the c-myc gene can be obtained as ATTC No. 41010 and manipulated in vitro to obtain these sequences using conventional techniques well known in the art) to generate pHEBoSVmyc 1, 2, 3 (See FIG. 3), the complete c-myc gene. In pU3 2, 3 myc and pLIhmyc the EcoRl sites correspond to the original one located 3' to the human c-myc gene, while the 5' BamHI sites were obtained by polylinker addition to the original AluI and XhoI sites, respectively (see scheme in FIG. 1). To generate pHEBoEumyc 2, 3 (See FIG. 4), the 7Kb HindIII-EcoRI fragment from plasmid pKWI was ligated into the HindIII-BamHI sites of pHEBo after blunt-ending the EcoRI and BamHI sites using T$_4$ DNA polymerase. The plasmid pKWI was derived from the translocated c-myc gene of the Manca Burkitts lymphoma cell line.

EXAMPLE 4: TRANSFECTION OF EBV-INFECTED, SELECTED B-CELLS

Transfection was performed by electroporation essentially as described by Toneguzzo et al., *Mol. Cell. Biol.* 6:703, 1986, incorporated by reference. Briefly, cultures of cells were resuspended in 0.4 ml. of cold phosphate buffered saline (PBS) at a concentration of $2.5 \times 10^7$cells/ml. Plasmid DNAs (i.e., pHEBoSVmyc 1,2,3, pHEBoSVmyc 2,3 and pHEBumyc 2,3) were added to individual cell suspensions to obtain a concentration of about 5 picomoles in 0.4 ml in each separate culture. The cell-DNA suspensions were placed in an electroporation chamber and a high voltage (2.0 KV) pulse was applied (ISCO, Lincoln, Nebr.). The cell- DNA mixtures were then allowed to incubate at room temperature for seven minutes before being added to 1 ml of phosphate buffered saline containing 10% fetal calf serum (FCS). After seven minutes at room temperature the mixtures were added to 5 ml of warm growth medium (RPMI 1640, GIBCO, Grand Island, NY). Cell cultures were grown for 48 hours before selection in 300 microgram per ml of Hygromycin-B (Calbiochem., San Diego, Calif.) for three weeks.

The cells generated above grew in the presence of hygromycin, displayed a doubling time of 27 hours in suspension culture, produced IgM, grew in semi-solid agarose and propagated when injected into mice. Additional proof that these cells harbored the plasmids was obtained by Southern Blot hybridization performed as follows. Low molecular weight DNA was isolated by Hirt extraction (Hirt, B. *J. Mol. Biol.* 26:365–369, 1967). DNA was analyzed by the well known Southern blot hybridization technique using c-myc probes 32P-labelled by nick translation (specific activity $2-4 \times 10^8$ cpm/ug) Hybridization was performed in 50% formamide, $3 \times$ SSC 5x Denhardt's solution, 0.5% SDS at 37° for 16 hrs. Washing was performed in $0.2 \times$ SSC, 0.5% SDS at 60° for 2 hrs.

The transfected B-cells of the present invention may be cultured in conventional medium (RPMI 1640 supplemental with fetal calf serum) for secretion of human monoclonal antibodies of the desired specificity.

EXAMPLE 5: EBV-CMYC-PLASMIDS CONTAINING EBNA SEQUENCES

Figure 5:
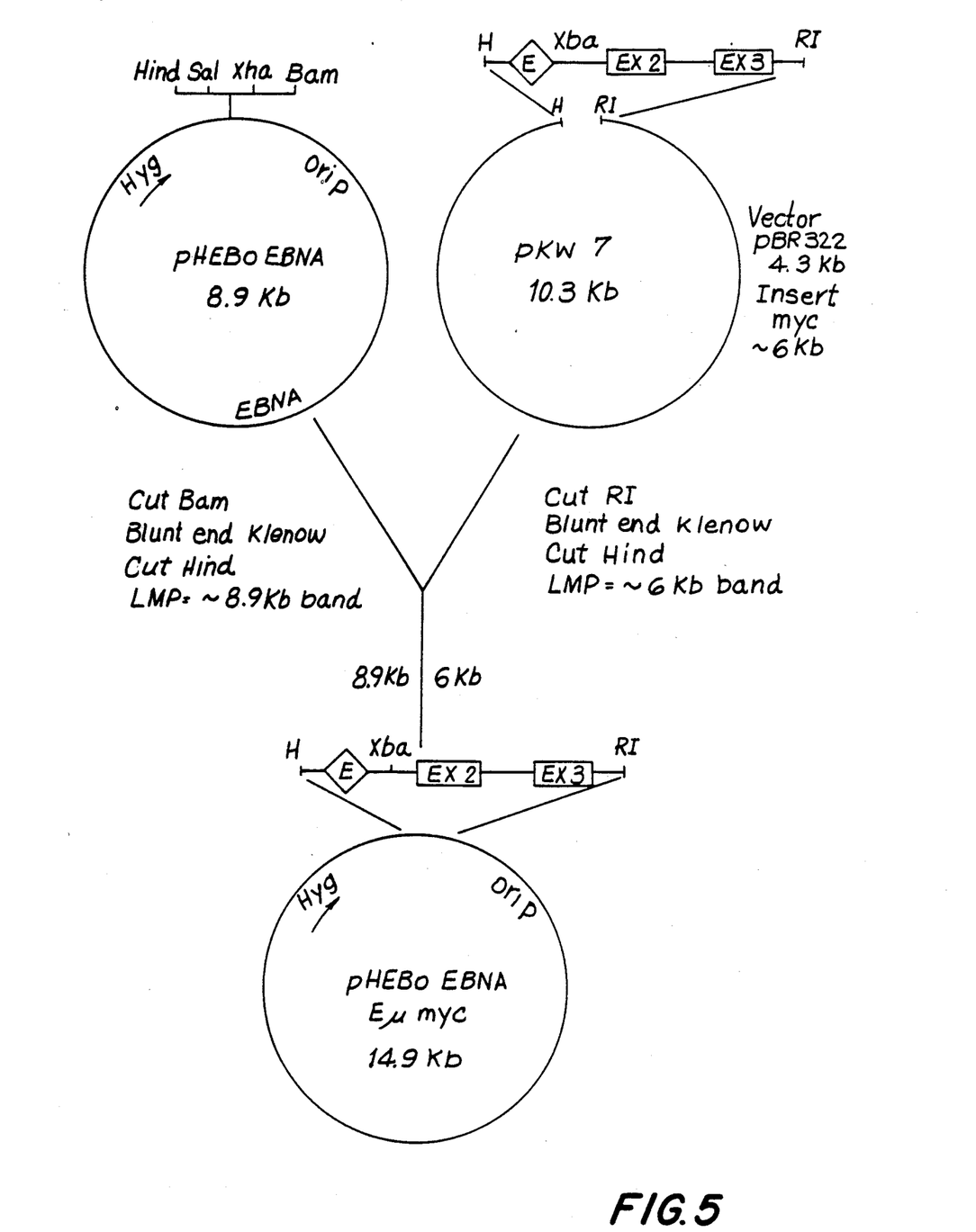
FIG. 5 is a schematic representation of plasmid pHEBoEBNA.
Figure 6:
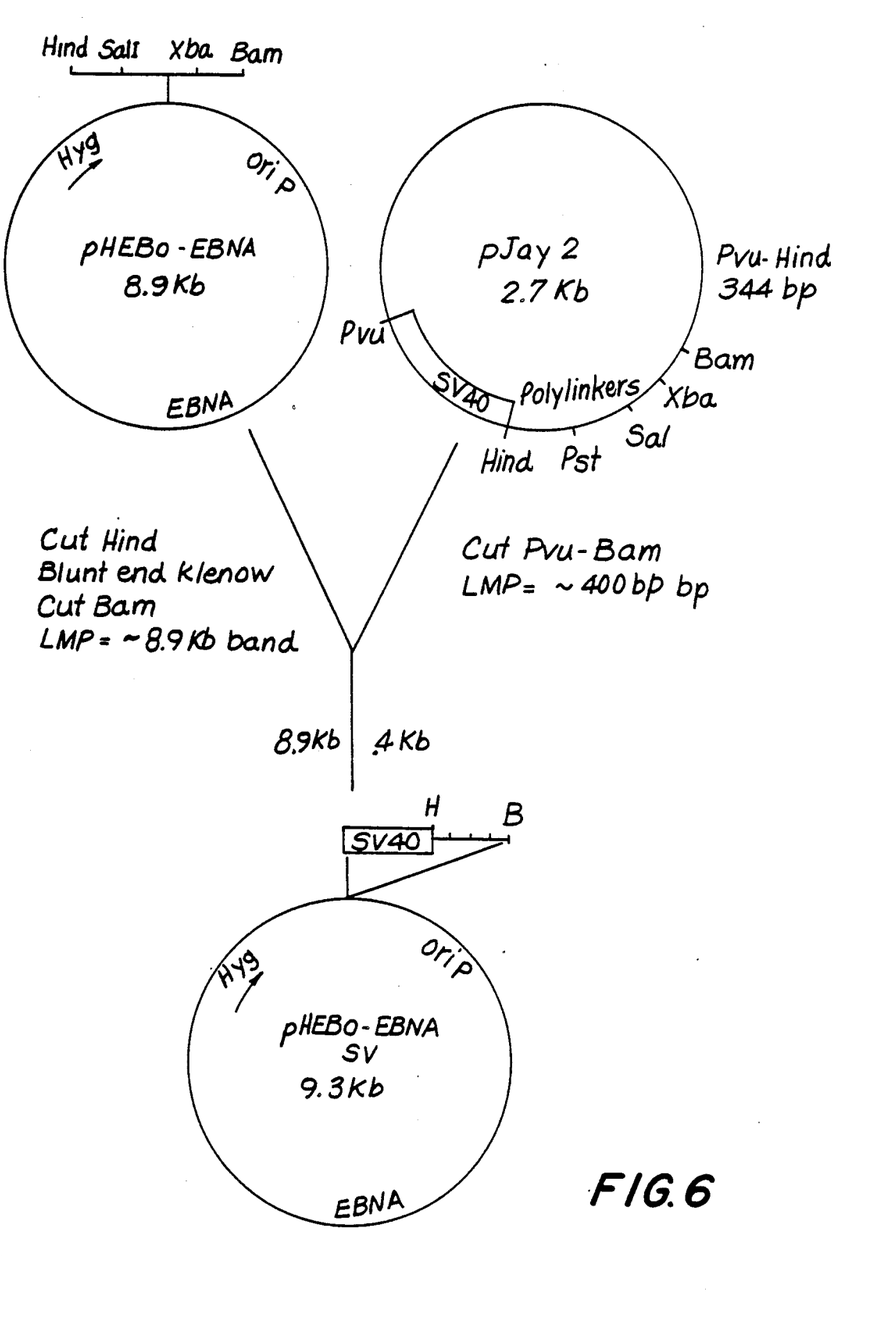
FIG. 6 is a schematic representation of the construction of plasmid pHEBoEBNASV.
Figure 7:
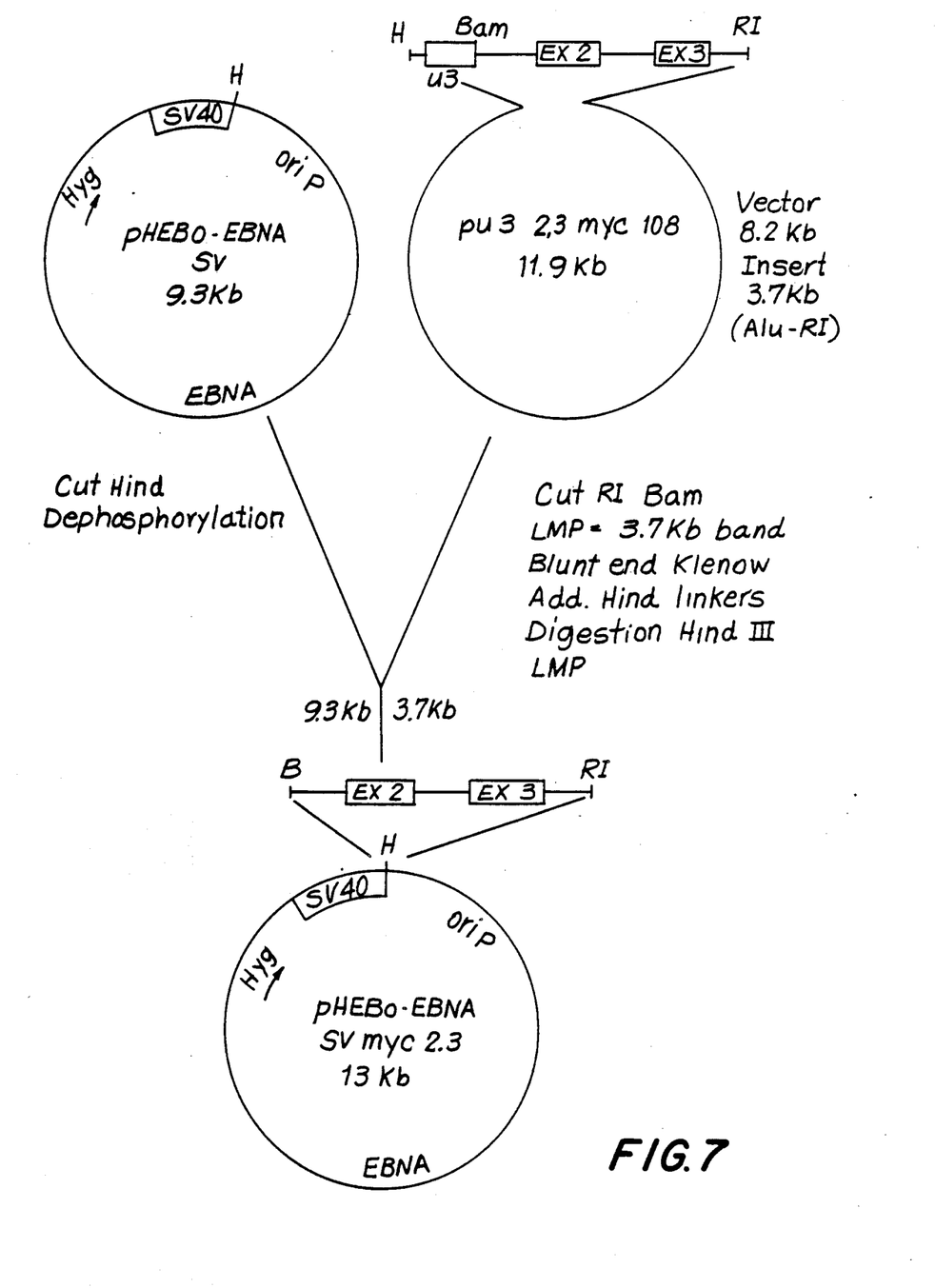
FIG. 7 is a schematic representation of the construction of plasmid pHEBoEBNASVmyc 2, 3.

In order to construct the pHEBoEBNAmyc 2,3 plasmid (See FIG. 6), a pHEBoEBNA plasmid was first generated (See FIG. 5) by ligation of a PvuII-BamHI fragment from the pJay plasmid into the HindIII (blunted by T4DNA polymerase) and BamHI sites of pHEBoEBNA. Then the same BamHI fragment from the plasmid pU3.2.3.myc used in Example 4 above was HindIII linkered and ligated into the HindIII site of pHEBoEBNASV, thus generating pHEBoEBNASV-myc 2,3.

The plasmid pHEBoEBNASV myc 2.3 was transfected into HeLa cells using the well-known calcium phosphate precipitation technique (Wigler, M. et al, *Proc. Nat. Acad. Sci. USA* 73:1373; 1979) or into human lymphocytes (not infected by EBV) by electroporation, as described in Example 4 above. The presence of the plasmid (and its expression) was documented by growth in selective media and Southern blot hybridization as above.

EXAMPLE 6: SCREENING FOR SPECIFIC B-CELLS USING FLUORESCENCE ACTIVATED CELL SORTING (FACS)

B-cells isolated as described in Example 1 above may be screened for their specifities as described in Casali, P. et al (op. cit., incorporated by a reference). Approximately $1 \times 10^6$ B-cells will be incubated for 35 minutes in ice-chilled sterile Hanks balanced salt solution without $Ca^2$ or $Mg^2$ and without phenol red containing 1% bovine serum albumin (BSA-HBSS) and appropriate amounts of biotinylated antigen. Typically, 1 mg/ml antigen will be incubated in 0.1 M sodium bicarbonate (pH 8.8) and 10% dimethylsulfoxide (DMSO) in the presence of 1 nanogram of d-biotin N-hydroxysuccinimide ester for 2 hours at room temperature. The cells may be washed with cold BSA-HBSS and then allowed to react with FITC (fluoricineisothiocyanate) avidin (FITC-avidin) ($1.56 \times 10^{-7}$M) in cold BSA-HBSS for 45 minutes. A small sample of B-cells ($10^6$) will be simultaneously incubated with BSA-HBSS devoid of biotinylated antigen and allowed to react with FITC-avidin under similar conditions. After further washing with cold BSA-HBSS, cells from both samples will be resuspended at a density of $10^6$ cells per ml in the same medium and at different times applied to a Becton and Dickinson Model 440 FCS with a 488 Argon laser (Becton and Dickinson, Mountain View, Calif.). Cells which fluoresce in the presence of biotinylated antigen and FITC—avidin are identified and isolated.

What is claimed is:

1. A method for preparing human monoclonal antibody producing cells, comprising the steps of:
   isolating human B-cells producing antibodies of a desired specificity,
   infecting said human B-cells with Epstein-Barr Virus recovering said Epstein-Barr Virus-infected B-cells,
   transfecting said recovered Epstein-Barr Virus infected human B-cells with a vector containing an activated c-myc gene capable of constitutive expression and having a selectable genetic marker, and
   recovering said Epstein-Barr Virus-infected c-myc-transfected malignant transformed B-cells.

2. The method of claim 1 wherein said c-myc containing plasmid is a member selected from the group consisting of pHEBoSVmyc 1, 2, 3; pHEBoSVmyc 2, 3; and PHEBuSVmyc.

3. The method of claim 1 wherein said c-myc containing plasmid comprises a retroviral vector.

4. A method for obtaining transformed human B-cells comprising the steps of:
   collecting human B-lymphocytes from peripheral blood of a human subject,
   infecting said collected human B-lymphocytes with Epstein-Barr Virus,
   recovering said Epstein-Barr Virus-infected human B-lymphocytes,
   transfecting said virus-infected B-lymphocytes cells with an activated c-myc gene capable of malignantly transforming said B-cells and of constitutive expression and having a selectable genetic marker, and
   recovering said virus-infected, c-myc transfected human B-lymphocytes.

5. A method for producing human monoclonal antibodies which comprises:
   isolating a human B cell which produces an antibody directed against a specific antigen,
   infecting said isolated B-cell with Epstein-Barr Virus,
   transfecting said Epstein-Barr Virus infected B-cell with an effective amount for transfection of an activated c-myc gene capable of constitutive expression and having a selectable genetic marker, to form a malignant c-myc transfected human B-cell,
   recovering said Epstein-Barr virus infected, malignant c-myc transfected human B-cell, and
   culturing said transfected B-cell under antibody producing conditions.

* * * * *

UNITED STATES PATENT AND TRADEMARK OFFICE
CERTIFICATE OF CORRECTION

PATENT NO. : 4,997,764
DATED : March 5, 1991
INVENTOR(S) : RICARDO DALLA FAVERA

It is certified that error appears in the above—identified patent and that said Letters Patent is hereby corrected as shown below:

Title page, [54], delete the title and replace with

-- TRANSFORMATION OF HUMAN B LYMPHOCYTES WITH EPSTEIN BARR VIRUS AND MYC CONTAINING VECTORS --.

Signed and Sealed this

Twenty-eighth Day of July, 1992

*Attest:*

DOUGLAS B. COMER

*Attesting Officer*  *Acting Commissioner of Patents and Trademarks*